United States Patent
Doyle et al.

(10) Patent No.: US 6,291,823 B1
(45) Date of Patent: Sep. 18, 2001

(54) ION-INDUCED ELECTRON EMISSION MICROSCOPY

(75) Inventors: Barney L. Doyle; Gyorgy Vizkelethy, both of Albuquerque, NM (US); Robert A. Weller, Brentwood, TN (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/416,387

(22) Filed: Oct. 12, 1999

(51) Int. Cl.[7] ............................... G01N 23/00; G21K 7/00
(52) U.S. Cl. ..................... 250/308; 250/306; 250/310; 250/309
(58) Field of Search .................................. 250/308, 306, 250/310, 309

(56) References Cited

U.S. PATENT DOCUMENTS

| | | | |
|---|---|---|---|
| 4,829,243 | * 5/1989 | Woodard, Sr. et al. | 324/158 R |
| 5,451,783 | * 9/1995 | Coxon et al. | 250/305 |
| 5,990,476 | * 11/1999 | Larson et al. | 250/251 |

OTHER PUBLICATIONS

Ion Bombardment induced segregation effects in VDx studies by SIMS and SNMS, authored by Scholz et al., Journal of Alloys and Compounds, 253–254 (1997) pp. 459–462.*

Web Page of *Physics and Space Technology* home page—*Ion–Surface Interaction Studies*—Maintained by Joseph W. McDonald, mcdonald6@llnl.gov.

* cited by examiner

Primary Examiner—Jack Berman
Assistant Examiner—Kalimah Fernandez
(74) Attorney, Agent, or Firm—Timothy D. Stanley

(57) ABSTRACT

An ion beam analysis system that creates multidimensional maps of the effects of high energy ions from an unfocussed source upon a sample by correlating the exact entry point of an ion into a sample by projection imaging of the secondary electrons emitted at that point with a signal from a detector that measures the interaction of that ion within the sample. The emitted secondary electrons are collected in a strong electric field perpendicular to the sample surface and (optionally) projected and refocused by the electron lenses found in a photon emission electron microscope, amplified by microchannel plates and then their exact position is sensed by a very sensitive X Y position detector. Position signals from this secondary electron detector are then correlated in time with nuclear, atomic or electrical effects, including the malfunction of digital circuits, detected within the sample that were caused by the individual ion that created these secondary electrons in the fit place.

24 Claims, 4 Drawing Sheets

ION-INDUCED ELECTRON EMISSION MICROSCOPY

STATEMENT REGARDING FEDERALLY SPONSORED RESEARCH

This invention was made with Government support under Contract DE-AC04-94AL85000 awarded by the U.S. Department of Energy. The Government has certain rights in the invention.

CROSS-REFERENCE TO RELATED APPLICATIONS

Not applicable.

REFERENCE TO A MICROFICHE APPENDIX

Not applicable.

BACKGROUND OF THE INVENTION

This invention relates to a system for analyzing the effects of high energy ion radiation upon materials and the function of semiconductor electronic circuits, ion beam analysis. More particularly it relates to a system for correlating the impact point of an ion as a function of the mapped origination point of the secondary electrons that are emitted with the effect(s) of that ion upon the sample itself.

Nuclear microprobe analysis is currently performed by focusing MeV ions onto a sample and then scanning the ion beam in a flying spot analysis. The nuclear, atomic, or charge collection signals that are created by the interaction of the ions with the sample constitute the detected signal. The location from which the signal originates on the sample is known by the position of the scanning ion beam at the time the signal is created and detected. The position of the "flying spot" is derived from the scanning apparatus that moves the focussed ion beam spot back and forth across the sample. Analytical techniques using nuclear microprobe analysis have reached a 0.3–0.9 micron lower limit for the beam spot resolution with presently available magnetic and electrostatic focusing lenses. No significant improvements in spatial resolution have been reported in over 5 years. There are a variety of factors involved in this stagnation that include the difficulty in manufacturing the lenses for these ion beams with the required accuracy, the difficulty in achieving the required level of vibration isolation, and the difficulty in focussing ions with high magnetic rigidity and/or poor chromaticity originating from cyclotrons, linacs and older Van de Graaff style electrostatic ion accelerators. There is a present need in the art to improve the spatial resolution for this analysis technique, a need that will only become more critical as the feature sizes of microelectronic circuits continue to shrink. There is also a need to provide performance that is equivalent or better than the present state of the art at a greatly reduced cost.

BRIEF SUMMARY OF THE INVENTION

An order of magnitude improvement in spatial resolution is made possible by the present invention which comprises discarding the need for the precisely focussed and scanned ion beams of the prior art in favor of utilizing an unfocussed ion source instead. Instead of relying upon knowledge of where the prior art ion beam spot is via the scanning system at the time a radiation effect is detected, this invention precisely images the position of the secondary electrons emitted from the surface as a result of an interaction of an ion with the sample. This imaging is done with much of the hardware already employed with photon electron emission microscopes, with the phosphor screen thereof being replaced with a very sensitive X Y position detector to map the location of the point of emission of the collected secondary electrons from the sample surface. The timing of these emissions of secondary electrons at the mapped positions on the sample surface is correlated with the ion-induced signals from the device or material sample under test to match a particular ion interaction to a particular place on the sample.

Preliminary data from laboratory prototypes already have demonstrated lateral resolutions equivalent to the best available scanning ion beam systems and offer the potential for 10 to 20 times better resolution. The replacement of the very complex ion beam focussing/scanning systems in prior art machines with the projection imaging of the emitted secondary electrons with readily available electron focussing optics significantly reduces the costs involved in making the types of measurements done by this class of systems. Also, because this invention avoids ion focusing, certain ion microbeam analyses previously limited to applications involving complex, large and expensive particle accelerators can be performed using simple, small and inexpensive radioactive alpha particle sources.

DETAILED DESCRIPTION OF THE INVENTION

Figure 1:
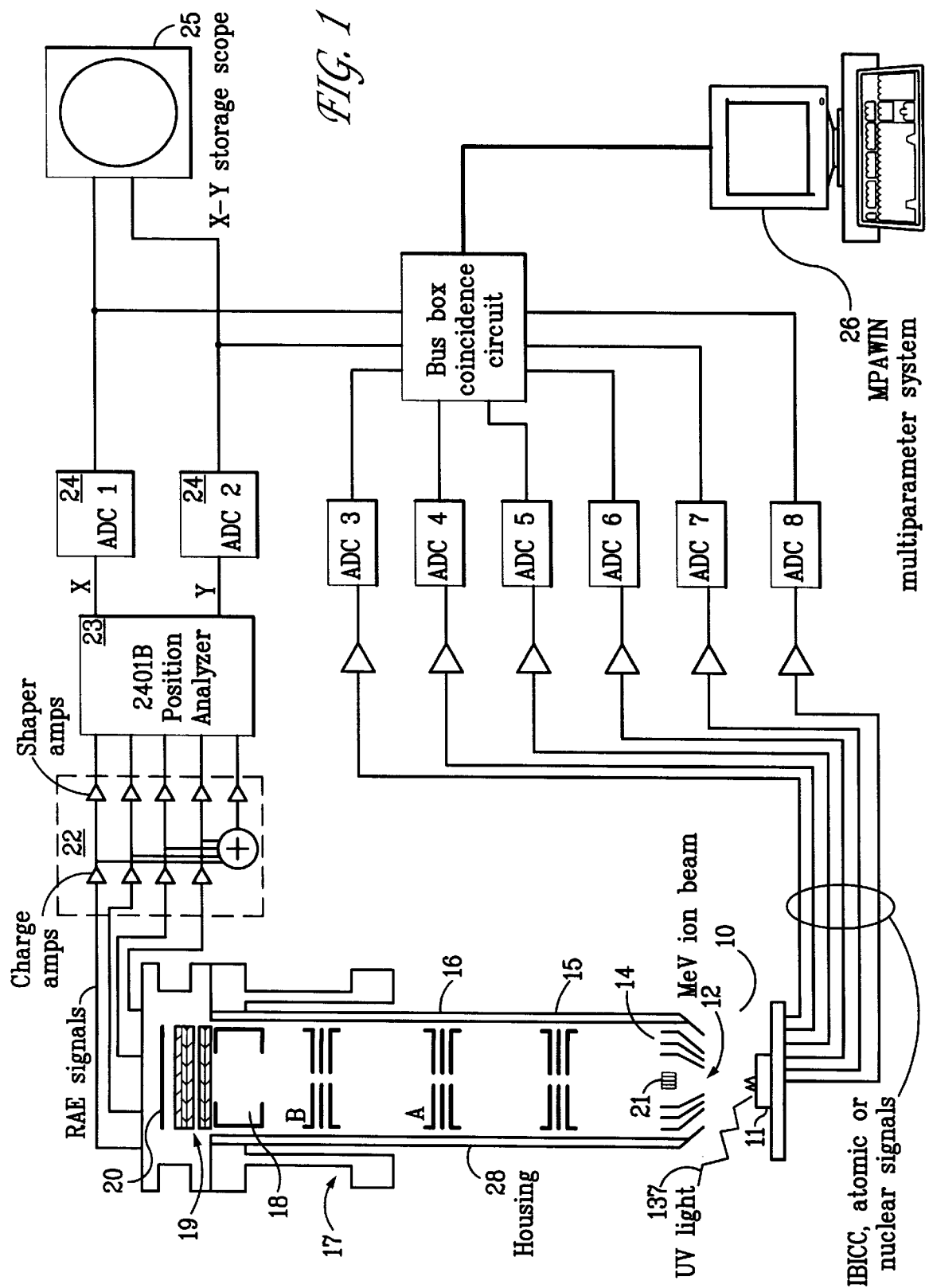
FIG. 1 is a schematic diagram of the various elements of the invention.

The signal produced by the emission of secondary electrons (SEs) from a sample bombarded by high energy (MeV) ions has been used for many years on conventional nuclear microprobes for focussing and identifying a target sample's region of interest. For these purposes the secondary electrons are not imaged. They are merely detected using channeltrons or similar detectors that amplify the secondary electrons collected across the whole sample surface impacted by the high energy ions. Actual projection imaging of emitted secondary electrons and ejected ions has been developed at the Electron Beam Ion Trap (EBIT) facility at Lawrence Livermore National Laboratory in a new type of time-of-flight microscope system that uses highly charged but low energy incident ions (in contrast to the high energy ions used herein). This particular use of projection imaging of secondary electrons is not, however, used to correlate the precise location of individual ion impacts with associated effects caused in the sample by the ion interaction, nor is the LLNL system proposed for high energy ions (MeVs or for general ion beam analysis application such as backscattering. It is only proposed for Secondary Ion Mass Spectroscopy.

As to the physics of secondary electron production, their emission is thought to involve three stages: 1) ionization by the incident ion and/or energetic secondaries, 2) successful transport of these liberated secondary electrons (SEs) to the surface, and 3) emission into the vacuum by overcoming a surface potential barrier. In the theory of Sternglass (see, E. J. Sternglass, Phys. Rev. 108 (1957) 1.), one assumes that if all the electrons ionized (through electronic collisions with the projectile) within the mean-free-path (MFP) of electron scattering from the surface reach the surface, then:

$$\gamma = P(\lambda/\cos(\theta))(dE/dx)/W, \quad (1)$$

where $\gamma$ is the SE yield per incident ion, $\lambda$ is the MFP for electron scattering, $\theta$ is the beam's angle of incidence, $dE/dx$ is the electronic stopping power of the incident ion in the target material, $W$ is the ion energy required to ionize an electron, and $P$ is the probability that the electrons reaching the surface can penetrate the potential barrier. The release depth $\lambda$ is thought to be very shallow (~1–5 nm) for metals but much larger for insulators and has a cosine angular distribution. The energy distribution is peaked at a few eV, and the shape of this distribution is independent of ion and its energy. The peak energy is only slightly higher than that observed for photoelectrons induced by a Hg lamp.

If one separates equation (1) into the parameters of the beam vs. those of the material:

$$\gamma = \Lambda(dE/dx)/\cos(\theta). \quad (2)$$

Hasselkamp et al. (Nucl. Instrum. and Methods 180 (1981) 349) have shown that $\Lambda$ ranges from 0.07 to 0.13 for smooth silver targets when the stopping power is expressed in units of eV/A. $\Lambda$ can be reduced significantly due to the presence of surface structures which perturb the uniformity of the local electric field.

The discussion will now turn to the details of construction of one embodiment of the invention. Variations from and substitutions for the various individual components in this system will be apparent to those of skill in this art. The Ion-induced Electron Emission Microscope (IEEM) system has been installed as a new end station on a nuclear microprobe line of a 6MV Tandem accelerator located at Sandia National Laboratories in Albuquerque, N.Mex. Currently, this line is approximately 1.4 m in length from object to aperture slits, 40 cm from aperture slits to the quadrupole doublet ion lens (not used to precisely focus the beam, but rather to provide a flood beam that fills the field of view of the electron projection system), and another 40 cm from the quadrupole lens to the target. The line utilizes a Dyer Systems QL-300 magnetic quadrupole doublet lens (of the Martin design). As is discussed in the next section, the results disclosed herein were produced using the largest aperture setting on the photo-emission electron microscope (PEEM) lens (300 $\mu$m) with sample viewing fields up to 250 $\mu$m. Clearly, ion strikes that occur outside this field of view may produce ion beam analysis (IBA) signals from the target but no SE position signals. Therefore, in this IEEM configuration, the purpose of the ion lens is merely to focus the beam sufficiently to limit most ion strikes on the sample to within the field of view of the electron detector and not to create the very tightly focussed ion spot used in previous scanning systems. This is especially important for measurements that are sensitive to radiation damage, or other ion fluence effects.

The "unfocussed" beams used in this study were 3 MeV $H^+$ and 24 MeV $Si^{+5}$, and the targets, which are discussed below, were Si micromachines, Cu TEM grids, and Au-coated PIN Si diodes. The beam's angle of incidence $\theta$ was 75° for all experiments. The stopping power of the H and Si ions in the various targets ranged from 2.0 (H on Si) to 982 eV/A (Si on Au) using Ziegler scaling (Appl. Phys. Lett. 31 (1977) 544). Referring to eq. (2), and using $\Lambda = 0.07$ and $\theta = 75°$, the SE yield for ion-target combinations was expected to range from ~0.5 to 266 in these experiments.

An IEEM experiment is based on the well-known phenomenon that each ion strike to the sample produces one or more SEs from the near surface region of the target. These electrons are then used to determine the position of the ion strike using the electron lens system of a Photo Electron Emission Microscope to accelerate and project these electrons onto a high resolution X Y position sensitive detector (PSD). A schematic diagram of the ion beam-target-PEEM-PSD system is shown in FIG. 1. The PEEM-PSD portion of the system is contained in a housing 28.

The PEEM lens is mounted nearly vertically in the sample chamber, 75° from the axis of the unfocussed ion beam 10. Samples are mounted 75° off normal so that the PEEM detector is always perpendicular to the target 11, which is a requirement of the objective immersion lens. The entrance (input) aperture 12 to the PEEM is located approximately 4 mm from the sample. A high-intensity Hg UV lamp 13 is also mounted in the chamber in position to illuminate the sample and perform standard photon-emission electron microscopy. The target station also includes an ex-vacuo microscopic camera system, not shown, for viewing the sample.

The field of electron emission microscopy is approximately 40 years old and has been reviewed by several authors, most recently by Griffith and Engel (Ultramicroscopy 36, 1 (1991)). Emission microscopy in general is a direct imaging technique. In other words, the image is not formed by scanning or sequential composition; and, therefore, ideally suited for real-time observation. A wide variety of contrast generating mechanisms contribute to distinguish surface features on a submicron scale. The small energy of the electrons used to form the image accounts for the surface sensitivity of this technique. Ironically, while these contrast mechanisms provide the utility of techniques like PEEM, contrast is not desirable for IEEM experiments. This is because IEEM relies on this signal to only provide a measurement of the strike point of an ion. For this reason, the SE yield is the main consideration in an IEEM experiment, and it is actually best if this yield is high and constant across the sample.

The electron optical column (Staib 350 PEEM (Staib Instrumente GmbH, Langenbach, FRG) of the basic microscope is formed by several elements shown in FIG. 1: the objective lens 14, the zoom lens 15, two projective lenses A 16 and B 17, and finally the X Y position sensitive detector (PSD) 20. The magnification ranges from 160× to 1600× (when projector A is not used, the magnification increases to 8000×) which corresponds to a field of view between 250 and 25 µm. The magnification is set by adjustments to the zoom lens, focusing is performed with the objective lens, and projector B is adjusted so that the field of view fills the PSD.

The sample surface itself is part of the objective lens. This lens is basically an immersion lens formed by four electrodes (a tetrode lens), the sample surface and a three electrode lens. An accelerating field of the order of several kilovolts per millimeter is applied between the sample and the first element of the lens (transfer voltage). The field strength is a key figure to determine the best lateral resolution. Keeping the sample at ground or at least near ground potential simplifies handling and current measurements; however, it also requires that the whole column is at the transfer potential (up to 15 kV in our case). The homogeneous electric field between the sample and the first lens electrode accelerates the electrons and forms a virtual image below the sample surface. The three electrode lens forms a magnified real image behind the objective lens.

The zoom and two projector lenses account for the final magnification on the image detector. An aperture in the source plane of the projector B limits the field of view. This aperture is useful to limit the area of the sample where SEs are produced and also to protect other areas from ion induced damage (particularly important for testing semiconductor electronic circuits) but is not needed in many cases. The zoom lens is used to set the total magnification. Two imaging modes are accessible; a low magnification mode and a high magnification mode. High magnification mode means a high field strength in the zoom lens. In this mode, the objective lens forms a real magnified image in front of the zoom lens, which is further magnified onto the aperture of projector lens B. Low magnification mode means a low field strength in the zoom lens. In this case, there is no real but only a virtual intermediate image formed. Switching between the imaging modes accounts for a flip in the observed image.

The sensitivity of the microchannel plate detector is reduced for higher energy electrons. To improve this sensitivity, a decelerating lens 18 that decelerates the electrons to ~1 keV is introduced between the final projector lens 17 and the position detector 20.

The most prominent factors limiting spatial resolution are lack of mechanical stability, astigmatism and aberrations. To ensure mechanical stability, the PEEM and its chamber sit on a vibration insulation system. Any deviations from cylindrical symmetry along the imaging column can introduce astigmatism. This symmetry is hard to maintain especially in the sample region. To counteract these effects, an octopole stigmator 21 unit is inserted near the back focal plane of the objective lens.

Figure 2:
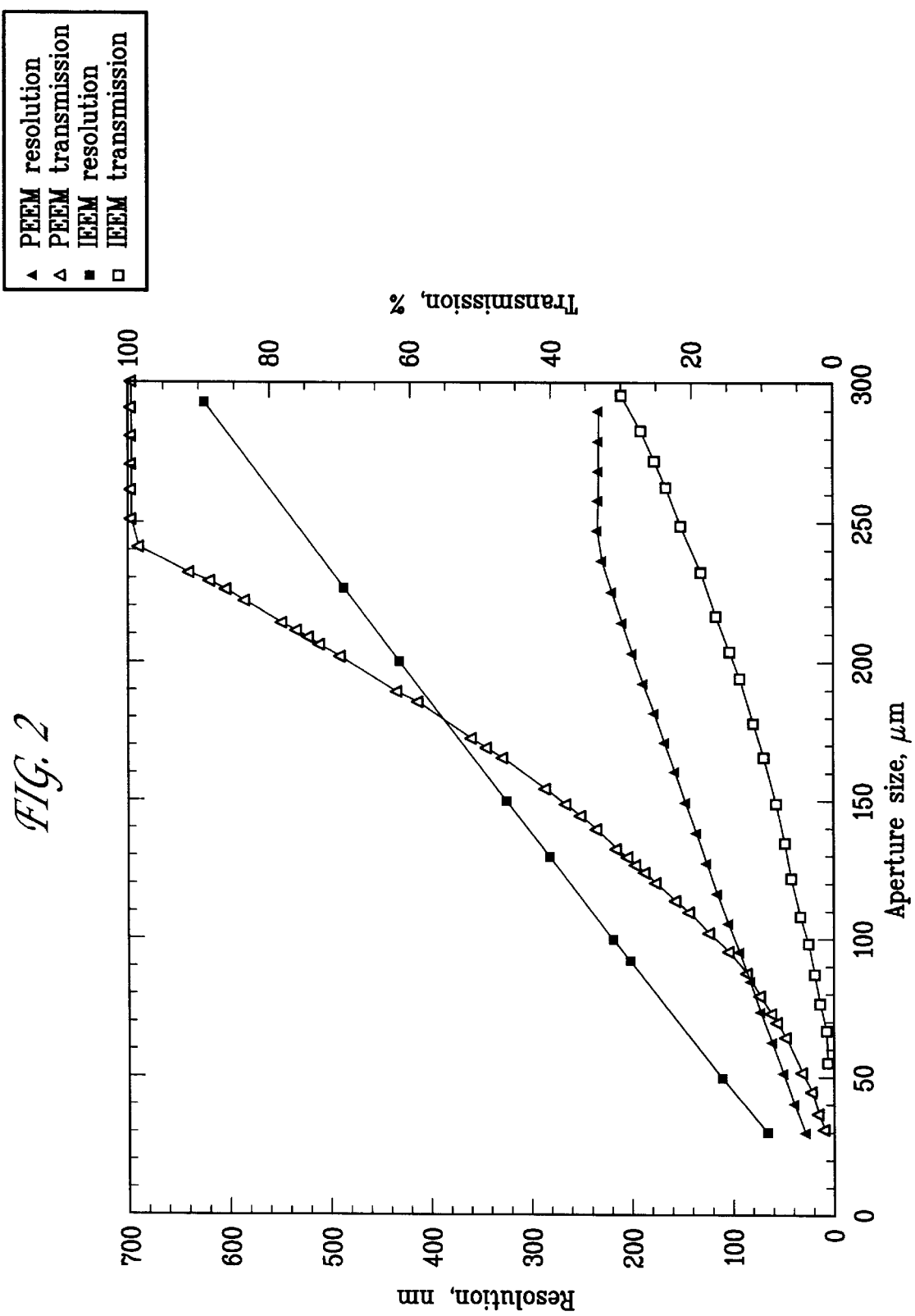
FIG. 2 is graph showing efficiency and resolution as a function of the diameter of the input aperture to the PEEM electron optical system for both photon induced secondary electrons and high energy ion induced secondary electrons, assuming electron mean energies of 1 ev and 5 ev respectively.

Due to the high field strength at the surface the acceptance angle for the electrons is nearly 90°. This gives rise to a rather large aberration disc or disc of least confusion in the virtual source region. To improve resolution, the total acceptance angle has to be limited by an aperture at the back focal plane of the objective lens. FIG. 2 shows plots of theoretical resolution (for chromatic aberration only) and transmission efficiency (using ray tracing) versus aperture size for this setup. For these calculations the energy distribution of SEs at the sample was assumed to be peaked at 5 (1) eV, have a 5 (1) eV FWHM for IEEM (PEEM), and be emitted in a cosine pattern. For the results reported below, a 300 µm aperture disc is used, and this should result in a resolution of 0.6 µm with a transmission efficiency of ~30% for IEEM, and 0.2 µm-resolution/100% transmission for PEEM. Use of a 50 µm aperture should improve the IEEM resolution to 0.1 µm with a corresponding loss of transmission to ~1% for IEEM.

Effective secondary electron detection and position recording is critical to the IEEM technique. The system poses several requirements including 1) the efficient detection of electrons, 2) 2-D imaging capability, and 3) time-resolution for the coincidence function and time-of-flight based measurements. A detailed description of this PSD is given in R. W. Odom, B. K. Furman, C. A. Evans, Jr., C. E. Bryson, W. A. Petersen, M. A. Kelly and D. H. Wayne, Analytical Chemistry 55 (1983) 574, which incorporated by reference herein in its entirety.

The X Y position detector head consists of a multi-stage, microchannel plate (MCP) electron multiplier 19 directly coupled to a charge-division position encoder 20 (resistive anode encoder, RAE). This position sensitive detector (PSD) was manufactured by Quantar Technologies (Quantar Technology Inc., Santa Cruz, Calif.), and a schematic of this detector is shown in FIG. 1 with the associated electronics. The MCP configuration used ensures the high electron gain (approx. $2 \times 10^7$) required for high position resolution (100 µm FWHM across 40 mm diameter active area) while maintaining a tight gain pulse-height distribution for single electron initiated events. A PSD resolution of 100 µm at the high PEEM gain of 1600× corresponds to a resolution at the sample of only 0.06 µm. Those skilled in the art will realize that a charge coupled device detector can be substituted for the RAE in many applications.

In operation, electrons impact the MCP surface located at the final image plane of the PEEM. This results in an electron cascade that is multiplied by the MCP to a measurable level and the resulting charge cloud is electrostatically focused onto the surface of the RAE encoder in an X-Y location corresponding precisely to the location of the incident event on the input MCP. The charge diffusing in the RAE is divided among four collection terminals in a ratio proportional to position in the X and Y axes. The output is fed to a four-channel charge-sensitive amplifier/shaper module 22.

From the ratio of the preamplifier output signals, the readout electronics (the Position Analyzer 23 shown in FIG. 1) computes the X and Y coordinates of each event. These coordinates are output as analog pulses where amplitude is proportional to position. In addition, the position analyzer contains discriminators and pulse-pile-up circuits to veto events that are too low or high in gain, or arrive too close together, to be properly imaged. The XY analog outputs are then connected to the external ADC's 24 used in a multiparameter data acquisition system and to a conventional analog variable persistence X-Y oscilloscope 25 to display real time SE images. The system used has a relatively high instantaneous dynamic counting range extending from the low count rate of the MCP background (10 cps) up to 100,000 detected events/sec (with random arrival statistics, corresponding to 4 usec dead time per event).

The detection efficiency of the MCP's is in the range of 55–80%, where the lower limit is determined primarily by the ratio of microchannel pores to interstitial web area. 100 psec FWHM time resolution for the PSD is obtained by an auxiliary MCP pickoff circuit which senses the time-of-passage of the single event through the MCP.

The detector X and Y outputs are digitized by ADC's and fed to two inputs of an 8 parameter MPA/PC multiparameter system 26 (see FIG. 1) produced by FAST ComTec GmbH, Munich (M. Bogovac, I. Bodanovic, S. Fazinic, L Kukee and W. Wilhelm, Nucl Instrum. and Meth. B89 (1994) 219). This system operates in list mode, capturing data octets of up to 13 bits of X, 13 bits of Y and the desired number of digital bits from the energy parameters obtained from the separate detectors used for IBA. These data octets are written to fixed disk memory in the PC as sequential data events and can be simultaneously histogrammed in RAM memory and displayed in real time. In addition, the data system offers full time-coincidence capability between parameters, so events are accepted only if they fall into defined time ranges on each parameter. The data collected are by passing only those signals from the PEEM and an IBICC detector which are in coincidence. For this case, a list of events $\{X, Y, E_{IBICC}\}$ is produced which is exactly the type of list currently used in conventional ion-beam induced charge collection (IBICC) measurements of semiconductor circuits.

The initial focus of the PEEM and the region of interest on the sample is found using the Hg lamp 13. The tilt angle of the target is set to obtain the greatest SE intensity using PEEM. Following these operations, the Hg lamp is extinguished, and the ion beam 10 is directed to the target, and the Martin lens is used to adjust the size of the beam to fill the field of view of the PEEM. The PEEM is then focused again using the secondary electrons produced by ion strikes. The electron focusing (both for PEEM and IEEM modes), ion definition, and ion beam steering is observed in real time on the XY storage scope. An unintended, but highly desirable feature, of IEEM is its simplicity. The first IEEM image on this system was obtained only a minute after the first beam was introduced into the chamber.

A number of samples were analyzed using the system of this invention. A number of 1000-mesh Cu TEM grids were mounted in a stainless steel target holder. These grids are considered only as very marginal focusing/resolution targets because of their complex shape and the resultant near-surface electric field nonuniformities. Nevertheless, they are convenient and continue to be used for focussing. The resolution of the IEEM image was 1.0 $\mu$m at high magnification using a 24 MeV $Si^{5+}$unfocussed beam. Similar results were obtained with a 3 MeV $H^+$beam. Several Si targets were also imaged with the IEEM system.

The next example is of a true coincidence-based IEEM ion beam analysis (IBA) measurement: Ion Beam Induced Charge Collection (IBICC) of a Au-coated Si PIN photo diode using 24 MeV $Si^{5+}$and 3 MeV $H^+$. Initial attempts at this experiment were with uncoated PIN diodes, but there was no measurable SE production from such a target in either the PEEM or IEEM modes. Si diodes have a thin passivation oxide on their surface, and the Hg lamp (~5 eV) cannot excite photoelectrons from $SiO_2$. Ion induced charging of this layer is suspected as the cause for the low SE signal for IEEM. For diodes with ~0.5 $\mu$m of Au deposited onto the surface, the SE signal was extremely intense both in PEEM and IEEM mode.

Coincidence intensity and mean energy plots were made for the 24 MeV Si beam (about 100 microns in diameter). The plots were able to reveal differences in the depth of the Au coating and the presence of a scratch in the Au coating that resulted in low SE emission. Another plot of the summed IBICC spectrum revealed an edge effect of greatly increased SE emission and also suggested different energy losses of the Si in the Au layer before entering the diode due to the presence of two distinct peaks.

Besides the convenience of these samples, another good reason for performing these IBICC measurements on PIN diodes as that they provide an easy way to measure the net system SE generation and detection efficiency of IEEM. This can be done for a variety of different beams and target materials so long as the beams are entirely contained within the field of view of the IEEM. With this condition observed, every incident ion will produce an IBICC signal, but not all ions will produce detected SEs. This is because 1) they were not produced at the target in the first place, 2) they were lost in transmission through the PEEM lenses, 3) they didn't produce a signal in the MCP, or 4) the MCP signal was outside the processing window of the position analyzer. The system efficiency (SE counts/IBICC counts) for this IEEM was plotted for several such measurements using the H and Si beams on the Au-coated diode. Using Eq. 2, we would expect 2 electrons to be made by each 3 MeV proton. Using the 30% transmission through the PEEM and 55% detection efficiency by the PSD, a system efficiency for $H^+$on Au should have been 33% which is somewhat higher than the ~10% value measured. For the 24 MeV Si beams on Au, 266 electrons are produced by each ion, and the efficiency should clearly be 100% (i.e., the system should detect at least one SE per incident Si ion). The measurement is ~80%, and is probably low due to reason 4) above and the loss of SE signal near the scratch in the Au coating. The signals can also be collected by a high frequency RF amplifier or a charge sensitive preamplifier, either then being connected to a transient digitizer to measure current transients. Other setups are possible, including conventional IC testers when the IEEM is used for those applications.

The success of IEEM as a new type of nuclear microprobe analysis depends on: 1) the number of SEs produced by each impinging ion; 2) the net system efficiency for detecting and recording the position of these electrons; and 3) the detected event probability of the IBA technique used in conjunction with the IEEM. The influence of these three requirements on the utility of IEEM as a new ion beam microscopy bears further discussion.

The SE emission yield $\gamma$ was found to vary greatly from sample to sample. All grounded metal samples produced copious SE signals, semiconductors such as Si provided adequate signals, but for insulators, virtually no SE signal was observed. In order to perform IBICC on the oxide-passivated PIN diode, it was required to deposit a thin Au layer onto the diode to produce a sufficient number of SEs required for this analysis. The coating did not affect this particular IBICC analysis; however, it is clear that the application of coatings to increase the SE signal will not work in all cases. For example, it is not clear how such a conductive layer would affect the operation and performance of an integrated circuit under IEEM-IBICC analysis. It is also easy to envision analytical uses of IEEM-IBA where the deposit of such a layer would cause elemental interferences with, for example particle induced x-ray emission (PIXE) or RBS signals. On-the-other-hand, there are clearly large classes of materials, such as all metals, where such a coating is not needed, and the IEEM-based IBA analyses should work quite well. Particularly attractive are IBA or charge collection measurements, which require high-energy heavy ions because these will produce several hundred SEs for each ion. This high SE yield will balance reductions in system efficiency expected for ultra high resolution IEEM.

The SE detection efficiency $\epsilon$, i.e. probability for an electron emitted from the target to be recorded by the PSD, should be 15–20% using the 300 $\mu$m aperture. We measured this probability to be ~5%, using protons on Au (protons produce 2 SEs off Au). The efficiency obtained in an IEEM should increase with use. This increase will enable the use of smaller objective apertures that are required to achieve better resolution. To obtain a 0.1 μm IEEM resolution, FIG. 2 indicates that a 50 μm aperture must be used, and this will decrease the system efficiency to below 1%.

When an ion generates a SE that is detected, it should have a relatively high probability φ of doing something in the sample that is detectable. In the case of charge collection measurements, this probability is unity if the region stuck by the ion is a reversed biased pn junction. This is because all ions produce electron-hole (or ion) pairs in semiconductors through the energy loss process, and these signals are all detectable using charge sensitive preamplifiers. This unity detected-event probability is the main reason we first applied IEEM using the IBICC technique. It also provided the best means to measure system efficiency.

Other IBA techniques which have φ=1 include scanning transmission ion microscopy and single event upset imaging of ICs. Unfortunately, most other IBA techniques involve scattering or recoiling collisions that are not usually very probable. These include the usual RBS and Si or He-beam elastic recoil detection (ERD), both which have $\phi \sim 10^{-4-6}$ even for major element detection. The event probability for PIXE ranges from $10^{-3}$ to $10^{-5}$. Au beam ERD and He RFS can have φ up to 1%.

The utility of IEEM appears to be limited to those techniques where the product γεφ is fairly high. Because the present PSD can only handle count rates up to $10^5$/sec, the count rate of detected IBA events in coincidence with detected SEs, i.e. the IEEM count rate, will be $\gamma\epsilon\phi 10^5$. This count rate will remain quite high for the various radiation effects microscopy techniques such as IBICC and SEU Imaging and the transmission energy loss measurements. For Au ERD and He RFS measurements, the count rate is predicted to be in the 100–1000 cps range, but for PIXE the count rate will not exceed 10 cps, which may be too low to utilize with the equipment used in this embodiment.

IEEM still offers numerous advantages to traditional flying-spot nuclear microprobe analysis, and almost all of these advantages stem from the simple fact that keV electrons are much easier to focus/project than the MeV ions used for scanning in the prior art systems. IEEM will potentially offer a 10×improvement in image resolution for heavy ion based radiation effects microscopy and IBA. IEEM is particularly attractive for applications on cyclotrons or linacs, which have traditionally been all but excluded from nuclear microanalysis because of poor beam quality.

The present 75° angle of incidence of the ion beam raises two problems: The spatial resolution in 1D degrades as the range of interaction of the ion beam increases. Further, the depth of interaction is only about 25 percent of the ion range because of the glancing incidence.

In order to overcome these limitations in our next accelerator-based IEEM system, the ion beam will travel through the PEEM column using an annular PSD. In this way the ion beam will be parallel to the normal of the sample surface and it will automatically result in an overlap of the ion irradiation spot and the field of view of the PEEM.

Although the embodiment above was concerned with IBICC for a semiconductor circuit element, a PIN diode, it has other applications in radiation effects microscopy including time resolved IBICC and analysis of single event Effects (SEEs) in integrated circuits. Samples can also be measured for the nuclear or atomic effects produced in a sample by a high energy ion using the IEEM system. These sorts of ion beam analysis (IBA) compositional depth analysis techniques include PIXE that measure the areal density of atoms in a solid and for which IEEM can provide a two dimensional composition map of the sample. Other forms of IBA (ERD, RBA, NRA) measure composition as a function of depth into the sample, and here the IEEM system would generate a three dimensional composition map. The technique will be most effective for IBA with a high event probability (i.e. collision cross section) such as heavy ion elastic recoil detection, particle induced x-ray emission and heavy ion backscattering. The high energy ions to be used with IEEM are of course not limited to only the $H^+$ and $Si^{5+}$ ions disclosed above. Au ions will also work well, as will a number of other ions. High energy in this context is meant to include ion energy levels at or above about 1 MeV.

Figure 3A:
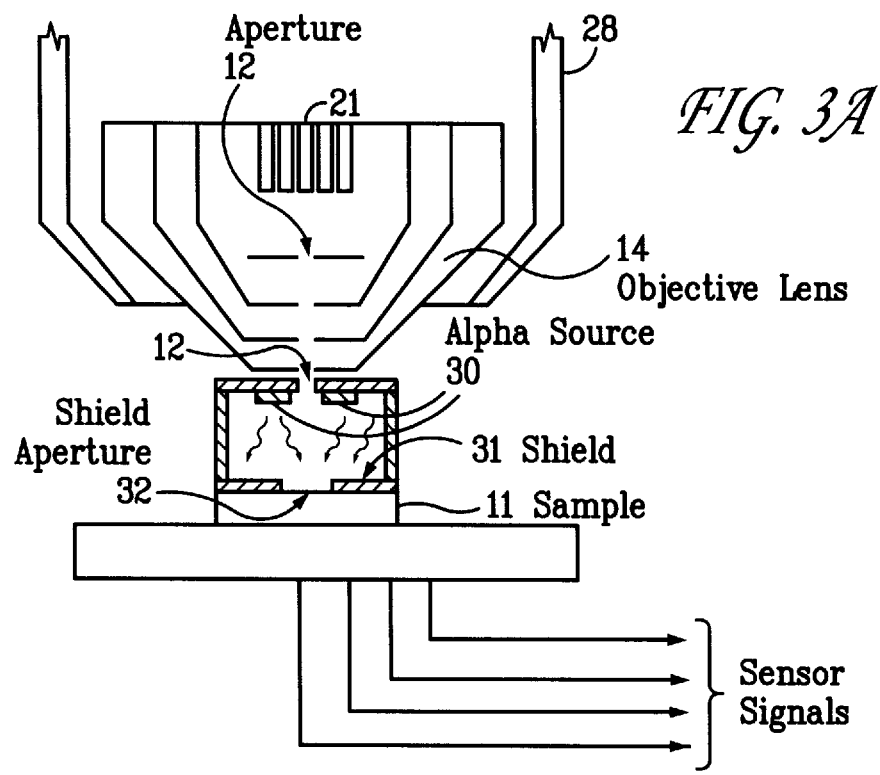
FIG. 3a is a diagram showing an alternative construction for the sample/input aperture portion of the system with the external ion beam source replaced with an integrated radiation source disposed about the input aperture and associated beam collimator and immediately below the PEEM.
Figure 3B:
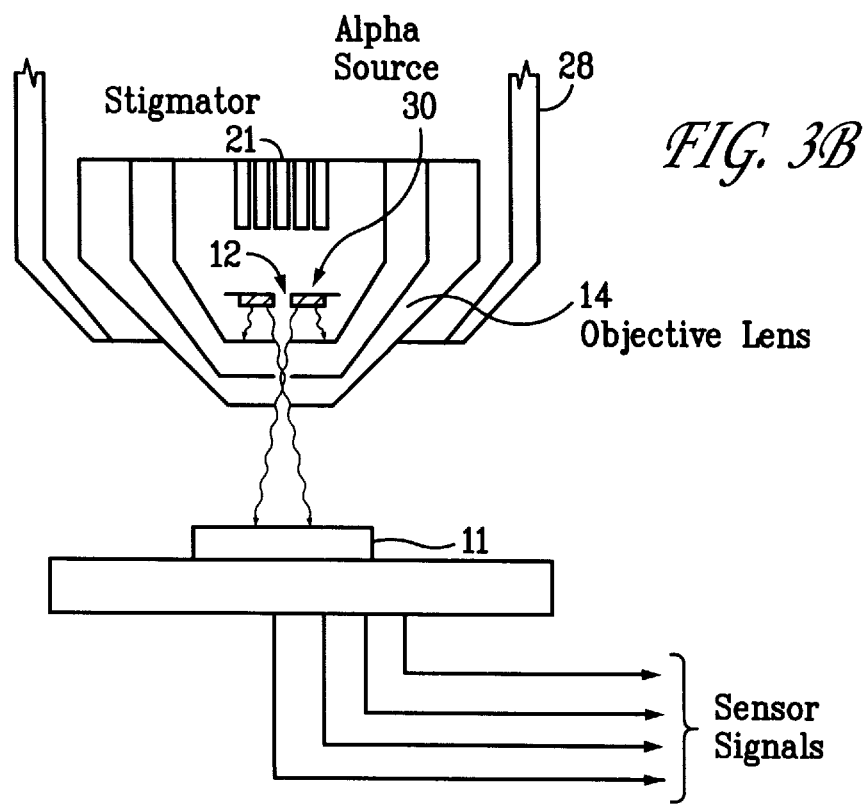
FIG. 3b is a diagram showing another construction utilizing a radiation source disposed about the PEEM objective aperture and within the PEEM.

An alternative approach being explored is to utilize an alpha particle (H+) source 30 arrayed at or about the perimeter of the input aperture 12 to PEEM electron optics as shown in FIGS. 3a and 3b. FIG. 3a also shows a shield 31 with a shield aperture 32 that protects most of the sample from damage from the alpha source 30 and prevents the generation of target-based IBA signals which cannot generate SEs detectable by the electron optics. Being external to the PEEM, the radioactive source is easy to change out. FIG. 3b shows an implementation wherein the alpha source 30 is internal to the PEEM. This implementation has the advantage that the radiation is confined within the PEEM.

Figure 4A:
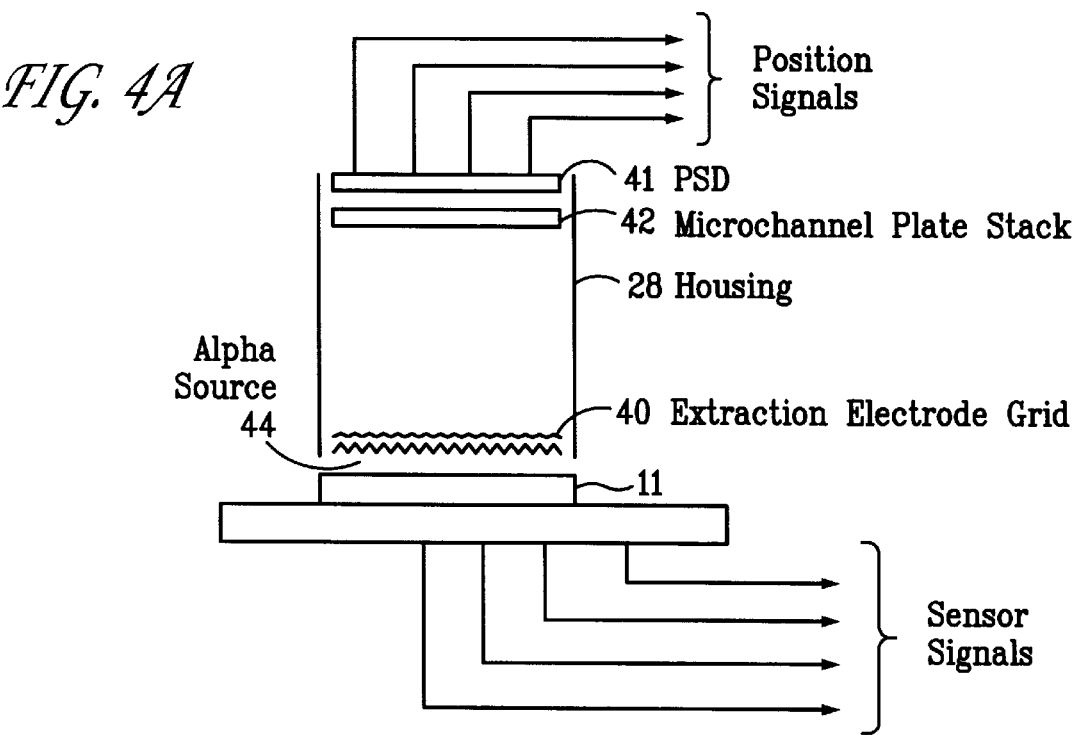
FIG. 4a is a diagram of another embodiment of the invention wherein a simple parallel plate extraction electrode grid replaces the PEEM electron projection system. This embodiment will have unity magnification and a large field of view. An accelerated ion beam would enter from the left or right of the sample, and if an radioactive source is used, it would be deposited on the extraction electrode grid.
Figure 4B:
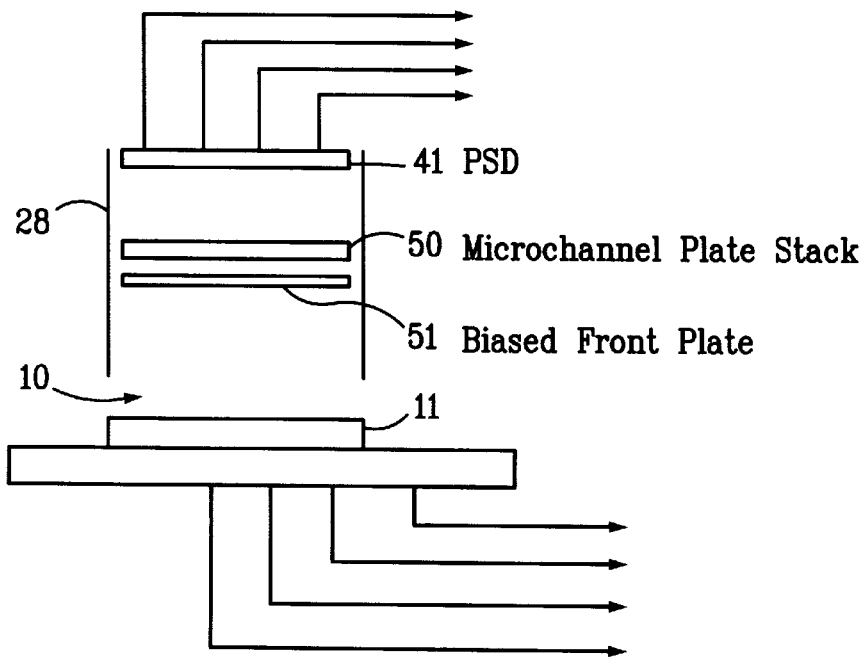
FIG. 4b is of an embodiment with the same characteristics as that in FIG. 4a, except that the extraction grid is not used, but rather, just the bias present on the front surface of the $1^{st}$ channel plate. If a radioactive source is used, it is deposited on this front channel plate with shielding to prevent radiation from entering this first channel plate.

Another two embodiments of an IEEM are shown in FIGS. 4a and 4b. Here a flux of unfocused alpha particles from a source, or any MeV ions from an accelerator strike a large area of a sample, equal in area to the size of the PSD. Instead of the electron optical lens (PEEM) discussed above, a simple extraction electrode 40 is used to pull SEs from the sample, direct them at ~normal incidence from the sample, and accelerate them to an energy easily detectable by the PSD 9~1 keV). The electrons then strike the MCPs 42 as before, but with only a unity magnification. The X Y resolution of such a system would therefore be equal to the position resolution of the PSD, which for the Quantar Detector is ~100 microns. Such low magnification IEEMs could find numerous applications inspecting charge collection in large regions, at moderate resolution, of fairly large semiconductors devices, such as radiation detectors. FIG. 4a shows an embodiment wherein the alpha source 44 is located on the side of an extraction electrode 40 facing the sample 11. FIG. 4b shows an embodiment wherein an ion beam 10 comes in from the side, and the secondary electrons are accelerated by a biased front plate 51. An alpha particle source could be substituted for the ion beam 10 if it were placed on the side of the biased front plate 51 facing the sample with sufficient shielding to protect the microchannel plate 50 from the alpha particles.

The invention now having been described, the reader will understand that any number of variations and changes may be apparent to one of skill in the art. The true scope of the invention is to be found in the claims appended below.

What is claimed is:

1. An apparatus for microscopically analyzing the interaction of high energy ions with a sample comprising:
   an unfocussed source of high energy ions directed at a surface of a sample;
   a sample from which ion-induced secondary electrons are emitted in response to impacts from the high energy ion and to which sensors are applied to measure another ion-induced effect other than the emission of secondary electrons from the surface on the sample;
   an electron projection system which refocuses individual ion-induced secondary electrons produced on the target sample by the ions, said system having an image plane;
   an electron position sensitive detector (PSD) placed at the image plane of the electron projection system which produces signals by which an origination point (x,y) of the secondary electrons and hence an impact point of each ion is determined;

a sensor means associated with the sample to detect the other ion-induced effect in the sample cause by the impact of an individual ion from the unfocussed ion source; and a correlator means to associate each secondary electron origination (and ion impact) point with each signal produced by the other ion-induced effect measured by the sensor in the sample by means of coincidence.

2. The apparatus of claim 1 wherein the high energy ions are ions having an energy of at least about 1 MeV.

3. The apparatus of claim 1 wherein the source of ions is a particle accelerator.

4. The apparatus of claim 1 wherein the source of ions is from a radioactive alpha particle emitter.

5. The apparatus of claim 1 wherein the electron projection system is an electrostatic lens system of a photo electron emission microscope (PEEM) to project the electron image at high magnification of from 10×–10000×.

6. The apparatus of claim 5 wherein the lens system includes a defining aperture and a first objective lens and the ion source is an alpha particle source placed proximate to the first objective lens.

7. The apparatus of claim 6 wherein the alpha particle source is placed at or near the defining aperture just behind the first objective lens.

8. The apparatus of claim 1 wherein the electron projection system is a simple biased grid electrode or a front biased surface of a channel plate to electrostatically project an image of the secondary electrons at near unity magnification.

9. The apparatus of claim 8 wherein an alpha particle source of claim is deposited onto the biased grid or onto a shielding means covering the surface of the channel plate so as to keep alpha particles from penetrating to the channel plate.

10. The apparatus of claim 1 wherein the sample is a semiconductor or insulator used in either an electronic device or radiation detector.

11. The apparatus of claim 1 wherein the PSD consists in part of multiple microchannel plates to amplify the secondary electron signal.

12. The apparatus of claim 11 wherein the PSD includes a resistive anode encoder as its final stage.

13. The apparatus of claim 11 wherein the PSD includes a charge coupled device as its final stage.

14. The apparatus of claim 1 wherein the sensor measures the current transient of each ion that strikes the sample.

15. The apparatus of claim 14 wherein the sensor is a high frequency RF amplifier followed by a transient digitizer which is electronically connected to the sample.

16. The apparatus of claim 14 wherein the sensor is a charge sensitive preamplifier followed by a transient digitizer which is electronically connected to the sample.

17. The apparatus of claim 14 wherein the sensor contains means to integrate the current transient and to provide a pulse whose height is proportional to the total charge collected following the impact of an individual ion.

18. The apparatus of claim 17 wherein the sensor is a charge sensitive electronic preamplifier which is electronically connected to the sample and followed by a spectroscopic amplifier to produce a pulse whose height is proportional to the collected charge following the impact of an individual ion.

19. The apparatus of claim 1 in which the sample is a semiconductor digital circuit and wherein the sensor includes means to determine the presence of a malfunction of the digital circuit and to provide an associated signal of this malfunction by the generation of a voltage pulse or other signal means.

20. The apparatus of claim 19 wherein the sensor is an IC tester adapted for measurement of broad beam single event effects testing of static or dynamic random access memories (SRAM or DRAM).

21. The apparatus of claim 19 wherein the sensor contains means for testing for malfunctions in the generation, modification or transfer of data through a microprocessor circuit elements.

22. The apparatus of claim 21 wherein the circuit element is a shift register.

23. The apparatus of claim 1 wherein the sensor detects radiation quanta (ions, high energy electrons, photons) produced by atomic or nuclear collisions caused when the ion strikes the sample and interacts with the atoms/nucleii therein.

24. The apparatus of claim 1 wherein the correlator means is a multiple analogue-digital-converter (ADC) based multi-parameter pulse-height analysis system.

* * * * *